United States Patent [19]
Walker

[11] Patent Number: 5,767,685
[45] Date of Patent: Jun. 16, 1998

[54] PORTABLE MICROWAVE MOISTURE MEASUREMENT INSTRUMENT USING TWO MICROWAVE SIGNALS OF DIFFERENT FREQUENCY AND PHASE SHIFT DETERMINATION

[76] Inventor: Charles W. E. Walker, 8651 Westminster Highway, Apt. 222, Richmond, British Columbia, Canada, V6X 3E3

[21] Appl. No.: 715,522

[22] Filed: Sep. 18, 1996

[51] Int. Cl.[6] ............................................. G01R 27/04
[52] U.S. Cl. ........................ 324/640; 324/632; 324/639; 333/260
[58] Field of Search ....................... 439/578; 333/24 R, 333/260; 324/640, 632, 639

[56] References Cited

U.S. PATENT DOCUMENTS

| | | | |
|---|---|---|---|
| 3,980,976 | 9/1976 | Tadama | 333/24 C |
| 4,229,714 | 10/1980 | Yu | 333/24 C |
| 4,399,419 | 8/1983 | Dobrovolny | 333/260 |
| 4,727,311 | 2/1988 | Walker | 324/640 |
| 4,797,120 | 1/1989 | Ulery | 333/260 |
| 4,962,384 | 10/1990 | Walker | 324/640 |
| 4,987,391 | 1/1991 | Kusiak | 333/24 C |

Primary Examiner—Ernest F. Karlsen
Assistant Examiner—Jose M. Solis
Attorney, Agent, or Firm—Klarquist Sparkman Campbell Leigh and Whinston LLP

[57] ABSTRACT

A portable microwave measurement instrument is disclosed for measuring an unknown property of a test material, such as moisture content, by generating and transmitting two microwave beams of different frequency through such material so a portion of the beam energy is absorbed by the moisture. The corresponding attenuated received signals are compared in order to compensate for the presence of a component in the test material, which is not being measured but which also absorbs microwave beam energy. A temperature compensation circuit using two thermistors is connected to the PIN diode attenuators to adjust their attenuation characteristics in compensation for changes in temperature. To determine the density of the test material, one of the microwave signals is used to measure the phase shift of the corresponding received signal and produce a phase shift output signal. Temperature compensation including another thermistor is also used to maintain the frequency of such one source substantially constant by changing the source voltage. Microwave signal connectors with high-pass characteristics are employed. The two attenuated received signals of different frequency and the phase shift output signal are combined in a signal processor to produce a percent moisture content signal.

20 Claims, 6 Drawing Sheets

PORTABLE MICROWAVE MOISTURE MEASUREMENT INSTRUMENT USING TWO MICROWAVE SIGNALS OF DIFFERENT FREQUENCY AND PHASE SHIFT DETERMINATION

BACKGROUND OF THE INVENTION

The present invention relates to the measurement of unknown properties of materials, such as moisture content or dielectric constant, using microwaves and in particular to a portable microwave instrument for the measurement of the moisture content of a material by transmitting microwave beams through such material so that a portion of the beam energy is absorbed by the moisture or other property. This percent moisture measurement is achieved with good accuracy in spite of the presence in the test material of another microwave absorbing property or component in variable amounts, by measuring attenuation using two beams of two microwave signals of different frequency and determining the density of the test material by measuring the phase shift of the received signal produced by one of such signals when its corresponding microwave beam is transmitted through the test material. The invention also includes a microwave antenna with two microwave signal connections for the two different frequency signals properly positioned in order to efficiently transmit or receive two microwave beams of different frequency with the same antenna without interference.

In addition, the present invention includes a temperature compensation circuit employing two thermistors, for each of two PIN diode attenuators that attenuate the received microwave signals in response to control signals in order to adjust the attenuation characteristics of the attenuators in compensation for changes in temperature. A second temperature compensation circuit including one thermistor is employed for maintaining the frequency of the microwave signal source used for phase measurement substantially constant by making compensating changes in the source supply voltage. Microwave signal connectors are employed in the portable microwave moisture measurement instrument to separate the outer conductors of interconnected microwave signal waveguides, such as coaxial cable connectors, to eliminate DC voltage coupling and to strongly attenuate low frequency modulation signals of 10 to 20 kHz but to allow low impedance AC voltage coupling at microwave frequencies with low attenuation. Also the test material is held in test containers of different sizes and an electrical sensor is provided to sense the size of the selected container using different patterns of conductive strips on each container and to produce a sensor output signal corresponding to the selected container size.

The present invention is especially useful in measuring the moisture content of various materials. In the previous U.S. Pat. Nos. 3,636,834, 3,818,333, 4,475,080 and 4,727, 311 of Charles W. E. Walker issued Sep. 19, 1972, Jun. 18, 1974, Oct. 2, 1984 and Feb. 23, 1988, respectively, and in the paper "Instrumentation For The On Stream Analysis Of Ash Content And Moisture Content In Coal Cleaning Plants" by Gunter Fauth, et al., published at the annual meeting of S.M.E. and A.I.M.E. at Los Angeles, Calif. Feb. 26 to Mar. 1, 1984, microwave moisture measurement apparatus is disclosed. However, these prior apparatus do not disclose a portable instrument using two microwave beams of different frequency to determine the amount of moisture attenuation of the microwave beams by the test material, by attenuation of the received microwave signals

2 using temperature compensated PIN diode attenuators with thermistors to adjust the attenuation characteristics and to measure the phase shift of one of the two attenuated received microwave signals to determine test material density for measurement of the percent of moisture content, in the manner of the present invention. In addition, they do not show a portable microwave moisture measurement instrument having microwave isolation connectors to isolate the outer conductors of interconnected waveguides from DC voltage coupling but allowing low impedance AC coupling at microwave frequencies. Furthermore, such prior patents do not disclose a portable microwave moisture measurement instrument in which the test material is held in test containers of different sizes and an electrical sensor is provided to sense the size of the selected container and produce a sensor output signal corresponding to the selected container size.

The invention is directed to the accurate measurement of the moisture content of a wide range of solid and liquid materials. Also the portable instrument can be used to measure electrical conductivity including the conductivity of ground water in pollution control equipment. In the above noted patents, it is shown that the absorption of microwave energy from a microwave beam transmitted through the material is capable of providing accurate information on its moisture content. The present inventor has found, however, that in all materials there are interfering effects or other factors present in the material, in addition to the amount of water present, which affect the microwave absorption.

All substances in the dry state produce some microwave absorption. In some, this microwave absorption is constant but in many of the materials which are industrially important, it is not constant and must be measured by an independent means if accurate measurement of moisture is to be obtained. In some cases, for example, the dry attenuation of the microwave is due to the dry substance being electrically conductive. If this is true in the macroscopic sense, the substance is probably not amenable to measurement by microwaves but many substances such as foundry molding sand and most coals are not electrically conducting in the macroscopic sense, yet contain microscopic particles or aggregates of atoms which are conductive and which, as a result, attenuate a microwave signal passed through the substance. In the case of both coal and foundry sand, this observed dry attenuation is thought to be due to elemental carbon particles, possibly in the form of small graphite crystallites. Finely divided metallic particles could have the same effect. Whatever the cause, the microwave attenuation due to such electrical conductivity is not frequency dependent, and so is markedly different from the water resonant absorption. The same is true of ionic conductivity which is another form of electrical conductivity and may arise from the presence of salts or of acids or bases in the substance being measured since any of these will dissolve in any water which is present to produce ions. Ionic conductivity will not contribute to dry attenuation but will affect the microwave attenuation so as to add to the moisture sensitivity in proportion to the ionic concentration. If this electrical conductivity of the dry material is not constant or the ionic concentration varies, then an independent measurement is needed to account for it if accurate moisture measurement is to be obtained.

In microwave moisture measurement, the microwaves are passed through the test material and therefore sense a certain volume of material and are absorbed in proportion to the number of water molecules in that sense volume. The measurement signal is therefore proportional to the mass of water per unit volume in the material. To express this as percent water requires that the mass of material in the volume sensed be known. This may require a measurement of the thickness or volume of material through which the microwaves are passed and the density of the material in that volume.

Yet another factor which affects the microwave moisture measurement readings is that some of the water present becomes bonded to the material. This may be physical, as for example Van Der Waals' forces. In either case, the water molecules so bonded are not free to rotate as free molecules and so do not exhibit the resonant interaction with microwaves. Except for hydrogen bonding of water to cellulose and starch molecules which produce a square law relationship between microwave attenuation and percent water, the present inventor found that almost all substances exhibit an interaction which appears to be a surface bonding phenomenon because it is dependent on particle size and particularly on the finest particles present. Thus, in pure silica sand there is effectively no bonding to a coarse grade but over 1% water bonds to 32 mesh grade sand. The net effect of the bonding in most substances, other than the organic ones mentioned above, is to halve the microwave attenuation up to the saturation level at which all the available bonds are satisfied. Beyond this point the attenuation becomes normal. For accurate moisture measurement through this saturation level, it is necessary that this level be known and that it be measured if it is not constant. This generally requires a knowledge of the fines content. Thus, in foundry molding sand it is the finely powdered Bentonite clay which establishes this level.

To eliminate these disturbing factors and for accurate moisture measurement, it is essential therefore that at least three independent measurements be made. Only in special cases, can some of these be replaced with constant subtractors or divisors or by periodic manual adjustments as, for example when lower accuracy is acceptable, or when measuring some substances such as ammonium phosphate fertilizer in which the ionic conductivity is directly proportional to the amount of water present and so may be accounted for by a constant calibrating factor. In some other cases where moisture determination is only required over a limited range of moisture which is known to be either wholly below or wholly above the level at which bonding is saturated, it may not be necessary to measure this level.

It is therefore the specific purpose of this invention to provide the additional independent measurement means, in addition to the simple microwave attenuation, which are needed as stated above to provide accurate moisture measurement.

The present inventor has determined that the effect of dry attenuation due to electrical conductivity can be eliminated by making microwave attenuation measurements at two different microwave frequencies. Because this dry attenuation is not frequency sensitive, the difference between the attenuation signals at the two different microwave frequencies is independent of such dry attenuation and depends only on the water present. This dual frequency measurement also eliminates the effect of variations in ionic conductivity when this is a concern. It is perhaps worth noting that there are some special cases such as alcohol and heavy water in which dry attenuation is frequency sensitive because these substances have their own resonant interaction with microwaves within the frequency range used for moisture measurement; clearly however, for this reason, microwaves cannot in any case be used to measure moisture in such substances unless another water resonance is available which is free of this restriction.

The present inventor has also determined that the density of the material in the microwave path can be measured using the same microwave beam as is used for one of the attenuation measurements by determining the change of phase of the microwave signal as it passes through the material. Like the attenuation, the phase change is a function of both the quantity of material in the microwave path and its content, but it is a different function so that both density and percent water can be computed. In effect, attenuation is proportional to the imaginary part of the dielectric constant $\epsilon_2$ of the material and phase change proportional to the real part $\epsilon_1$.

The dielectric constant $\epsilon$ of any material is a complex quantity as expressed by the equation:

$$\epsilon = \epsilon_1 + i\epsilon_2$$

Where $i$ is the square root of minus one. Both $\epsilon_1$ and $\epsilon_2$ are functions of both density and water content so that if density is constant, either attenuation or phase change could be used to measure percent water, but because the water resonance principally affects $\epsilon_2$ it is more sensitive to water and therefore generally preferred, particularly at low moisture levels. In the same way, at low moisture levels, $\epsilon_1$ is more dependent on density than on water content. Nevertheless, phase change can be preferred in some cases for moisture measurement, particularly when electric conductivity effects are strong because these do not affect $\epsilon_1$ and so do not interfere with phase change measurement.

The thickness or volume of material through which the microwaves are passed is often arranged to be held constant by the geometry of the sensing system but where this thickness or volume does vary it can readily be measured by a variety of well-known means such as by a linear resistive transducer or by a linear variable differential transformer.

The bonding saturation level is only required to be known where moisture measurements are required to be made through this level because it is only under those circumstances that two different moisture sensitivity slopes have to be used and their change over point must be known. The bonding saturation level is almost wholly dependent on the fines content of the material which, in many cases, is contributed by a single component of a mixture and the quantity of that component is known or can readily by measured by a standard technique. For example, in foundry molding sand it is the Bentonite clay which contributes the fines content and controls the bonding saturation level and a standard procedure exists for its determination.

It is also a significant part of this invention that if the measurement of the microwave phase change is not needed to determine the material density because the density is constant or is otherwise known, the phase signal can be used to measure bonding because some forms of bound water contribute the same as free water to $\epsilon_1$ but not to $\epsilon_2$, whence the microwave phase change is a function of total water, whereas microwave attenuation is a function only of free water.

The application of these ideas, leading to accurate moisture measurement is perhaps best understood by considering one specific case which will illustrate the method and has proved to be highly successful, namely the measurement of moisture in foundry molding sand. When the dry ingredients of such molding sand are first mixed, they cause only small microwave attenuation, but on coming in contact with hot iron, changes are produced so that when the sand is returned for re-use and its moisture content measured, it is found to attenuate the microwaves quite strongly, even when bone dry. This dry sand attenuation has been found to vary, in some cases considerably, from one batch of sand to another. The dry attenuation is, however, found to be independent of microwave frequency, at least over a two to one frequency range as for example between 10.7 GHz and 5.8 GHz and 2.45 GHz. The difference in the attenuations at the two frequencies is therefore independent of the dry sand attenuation and a function only of the water present. It is a function of the water present per unit volume and to present this as percent water it is necessary to divide by the sand density. Now the purpose for which the sand is used requires that it be highly compactable when prepared for use as molding sand. To achieve this, Bentonite clay is added to the sand which has the property that it swells when brought in contact with water. The density of foundry sand is therefore not constant and density measurement is necessary for accurate moisture determination by microwaves.

The bonding saturation level of the water in foundry sand is certainly dependent on the amount of Bentonite clay which is present in the mix, but so is the performance of the sand in its molding function; it is therefore the practice in all foundries to ensure that this is maintained and fresh Bentonite clay is added to achieve this. Provided the water measurement on return sand is done after the Bentonite clay has been so added as required, the bonding saturation level will be above the level of moisture occurring in the return sand so that measurement of this return sand by microwaves will not be affected by the bonding saturation level.

Thus, means to develop two microwave attenuation signals and one phase signal are necessary for accurate moisture measurement in foundry sand.

SUMMARY OF THE INVENTION

It is therefore one object of the present invention to provide a portable microwave measurement apparatus for accurately measuring an unknown property of a test material.

Another object of the invention is to provide a portable microwave moisture measurement instrument which is capable of accurate measurement of moisture content of a test material in the presence of another variable component which is highly absorbent of microwave energy.

A further object of the invention is to provide such an improved moisture measurement apparatus of greater accuracy which employs two microwave signals of different frequencies to compensate for the other variable component in the test material and temperature compensation of PIN diode attenuators used to attenuate the received microwave signals corresponding thereto by adjusting the attenuation characteristics of such attenuators to compensate for temperature changes.

An additional object of the invention is to provide such an improved moisture measurement apparatus which is capable of accurate measurement of the percent of moisture content even though the density of the test material varies by determining the phase shift of the received signal produced by a microwave beam transmitted through such test material.

Another object of the invention is to provide such an improved moisture measurement apparatus employing a temperature compensation thermistor for maintaining the frequency of the microwave signal source substantially constant by making compensating changes in the source supply voltage.

Still another object of the invention is to provide an improved microwave connector for separating the outer conductors of interconnected waveguides to eliminate DC voltage coupling and to strongly attenuate low frequency modulation signals but to allow low impedance AC voltage coupling at microwave frequencies.

A still further object of the invention is to provide such an improved microwave moisture measurement instrument using test containers of different sizes and an electrical sensor for sensing the size of the selected container.

BRIEF DESCRIPTION OF THE DRAWINGS

Other objects and advantages of the present invention will be apparent from the following detailed description of a preferred embodiment thereof and from the attached drawings of which.

DESCRIPTION OF THE PREFERRED EMBODIMENTS

In order to obtain accurate microwave measurement of moisture it has been found to be necessary, in most test materials to make two attenuation measurements with two different microwave frequencies simultaneously and to measure changes in the phase shift of one of them thereby giving three independent measurement signals which are suitably combined in a data processor such as an analog or digital computer to give the moisture content percentage. These measurements are done on test material 1, such as foundry sand, supported in a testing station 2 surrounded by microwave shields 3 such as by holding the material in a cup-shaped test container 4. Two microwave antennas are provided on opposite sides of the test container. One of the antennas is a transmitting antenna which transmits a beam of microwaves through the test material to a receiving antenna to test a property of the material, such as its moisture content, by determining the amount of microwave beam attenuation due to microwave energy absorption by such moisture or the other property tested.

Figure 1:
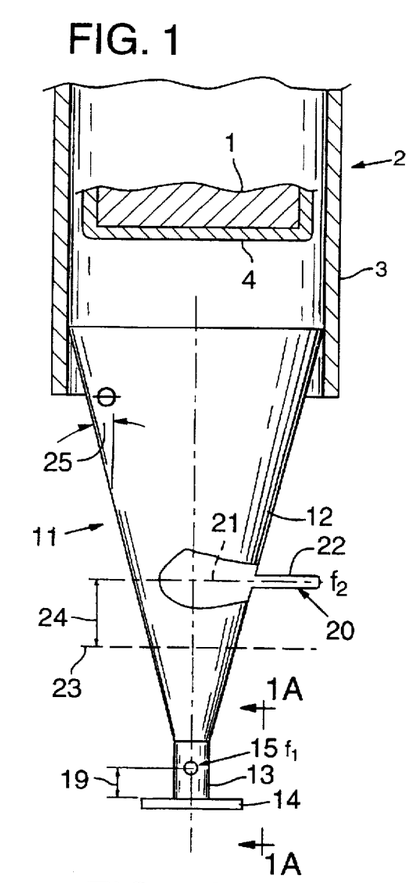
FIG. 1 is a side elevation view of the dual frequency antenna developed for use in one embodiment of the present invention with parts broken away for clarity.
Figure 1A:
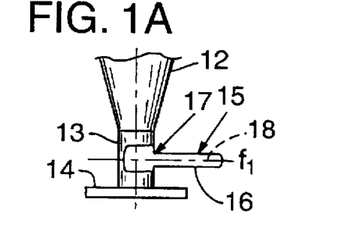
FIG. 1A is a partial elevation view taken along the line 1A—1A of FIG. 1.

In the preferred embodiment of this invention, a single transmitting antenna 11 shown in FIG. 1 is used to direct both microwave beams of different frequency through the test material to be measured and a second similar antenna is used to receive both beams. As shown in FIG. 1, the antenna 11 consists of a thin walled conical section 12 and short cylindrical section 13 made of metal or other electrically conductive material and containing a dielectric material. The cylindrical section is closed at one end by a metallic base 14. The higher frequency microwave signal, $f_1$, is fed in through a first coaxial connector 15 with its outer conductor 16 joined electrically to the cylindrical section 13 by soldering at joint 17 and with its center conductor 18 continuing to the center line or longitudinal axis of the antenna, as shown in FIG. 1A. The diameter D of the short cylindrical section 13 is related to the microwave frequency by the requirement that it be greater than the "cut off" diameter $D_c$, for that frequency given by:

$$D_c = \frac{C}{1.70645 f_1 \sqrt{\epsilon_1}} \quad \text{Equation 1}$$

Where C is the velocity of light in vacuum, $f_1$ is the frequency of the microwave signal and $\epsilon_1$ is the real part of the dielectric constant of the material filling the cylindrical section. The point at which the coaxial conductor 15 is located along the length of cylindrical section 13 is such that the distance 19 to the closed end of the cylinder is a quarter wavelength, $\lambda_G/4$ where $\lambda_G$ is the wavelength of the microwave of frequency $f_1$ inside the cylinder which is given by the formula:

$$\lambda_G = \frac{C}{\sqrt{\epsilon_1} \sqrt{f_1^2 - f_c^2}} \quad \text{Equation 2}$$

where $$f_c = \frac{C}{1.70645 D \sqrt{\epsilon_1}}$$

These two equations can be combined to give:

$$\lambda_G = \frac{1.70645 \, DD_c}{\sqrt{D^2 - D_c^2}} \quad \text{Equation 3}$$

From which the requirement that D be greater than $D_c$ is apparent.

The lower frequency $f_2$ of the two microwave frequencies is fed into the antenna 11 through a second coaxial connector 20 including an outer conductor 22 joined in the same way as coaxial conductor 15 and with its center conductor 21 similarly extending inward to the center line of the antenna. The point at which the coaxial connector 20 is located along the length of the antenna is required to meet the following conditions. There is a point along the conical section, indicated by the dashed line 23 at which the diameter of the cone is equal to the "cut off" diameter $D_c'$ for the lower frequency $f_2$ given by:

$$D_c' = \frac{C}{1.70645 f_2 \sqrt{\epsilon_1}} \quad \text{Equation 4}$$

This means that microwaves of frequency $f_2$ cannot be transmitted without loss along the small diameter part of the cone. Thus, the cone portion at position 23 acts in effect like an electrical open circuit. The coaxial connector 20 is required to be located a distance 24 outwardly from this open circuit position 23 such that this distance 24 is a half wavelength, $\lambda_G'/2$ where $\lambda_G'$ is the wavelength of the microwave frequency $f_2$ inside the cone. This wavelength $\lambda_G'$, varies along the distance 24 as the cone diameter varies. Integration over this distance gives the value L for the distance 24, from the equation:

$$L^3 = \left[ \frac{1.70645 D_c'}{2} \right]^2 \left[ L + \frac{D_c'}{\tan \theta} \right] \quad \text{Equation 5}$$

Where $\theta$ is the cone angle shown at 25 in FIG. 1.

The coaxial conductors 15 and 20 are spaced 90° apart around the cone circumference, as indicated in FIGS. 1 and 1A so that the plane polarized microwave beams of signal $f_1$ and $f_2$ have their respective planes of polarization at right angles. In this way the receiving antenna, which is identical to the transmitting antenna shown in FIG. 1 can be oriented so that the higher frequency $f_1$ is received only by its coaxial conductor 15 and the lower frequency $f_2$ is received only by its coaxial conductor 20. In this way, the two signals are kept distinct and separate and do not interfere with each other.

The antennas may be filled with air as the dielectric so that $\epsilon_1$ is approximately equal to 1, but in applications where they are transmitting directly into and receiving directly from a test material of higher dielectric constant, they may with advantage be filled with a dielectric of about the same dielectric constant $\epsilon_1$ as that of the test material, thereby improving the antennas radiating efficiency or enabling a smaller diameter antenna to be used. For example, to measure foundry sand using $f_1=10.7$ GHz and $f_2=5.8$ GHz, the present inventor has successfully used antennas 5½" long with outer diameter of 3" and with the cylindrical section being of ⅜" diameter using a dielectric material to fill the antennas having a dielectric constant $\epsilon_1$ of 3.8.

As already stated, the same antennas used for attenuation measurements can also provide the sensing elements for measurement of phase change to provide a more compact measurement apparatus. But, whereas, two microwave signals at the two different frequencies are used and combined to provide the attenuation measurement, only one microwave signal is used for phase measurement, and with special microwave components to separate and analyze the signal for phase. The use of a single transmitting antenna and a single receiving antenna for all three measurements is an important feature for accuracy because it ensures that all three measurements are made at the same location at the same instant of time.

Figure 2:
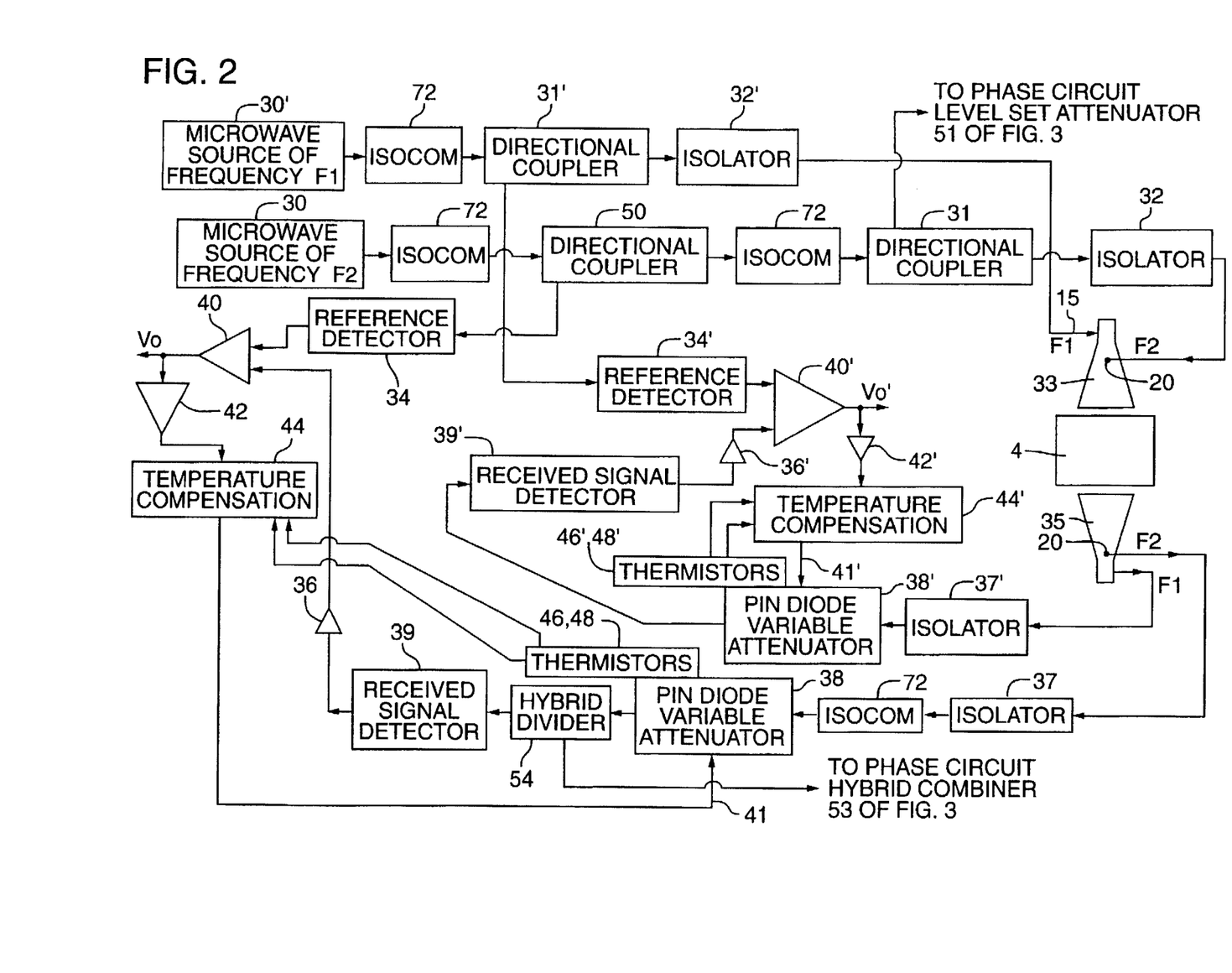
FIG. 2 is a schematic diagram showing the electrical circuit of the preferred embodiment of a portable microwave moisture measurement instrument for the measurement of microwave attenuation by moisture in a test material at two different microwave frequencies to determine its moisture content.

FIG. 2 is a schematic block diagram which shows the microwave devices and other electronic components in the preferred embodiment of the microwave measurement apparatus of the invention, which are used to generate output signals Vo' and Vo proportional to attenuation of the microwave beam by the test material for each of the two frequencies $f_1$ and $f_2$ in accordance with the formulas:

$$a' = K_1 W d + K_2 d \quad \text{Equation 6}$$

$$a = K_3 Wd + K_2 d \quad \text{Equation 7}$$

Where a', a are the attenuations in decibels for the two frequencies $f_1$ and $f_2$, and where $K_1$, $K_2$, $K_3$ are constants, W is percent water and d is density of the test material. In FIG. 2, a first microwave source 30' generates an amplitude modulated microwave signal of a high frequency $f_1$ of, for example 10.7 GHz which passes through a directional coupler 31' and an isolator 32' to connector 15 of a transmitting antenna 33 which is like antenna 11 in FIG. 1. A second microwave signal source 30 of a lower frequency $f_2$ of, for example 5.86 GHz transmits such signal through two directional couplers 50 and 31 and an isolator 32 to connector 20 of the transmitting antenna 33. The directional coupler 50 feeds a small part, generally between 0.1% and 1.0% of the signal $f_2$ to a reference detector 34 which produces a reference signal whose amplitude is proportional to the microwave power passed to the transmitting antenna.

Figure 11:
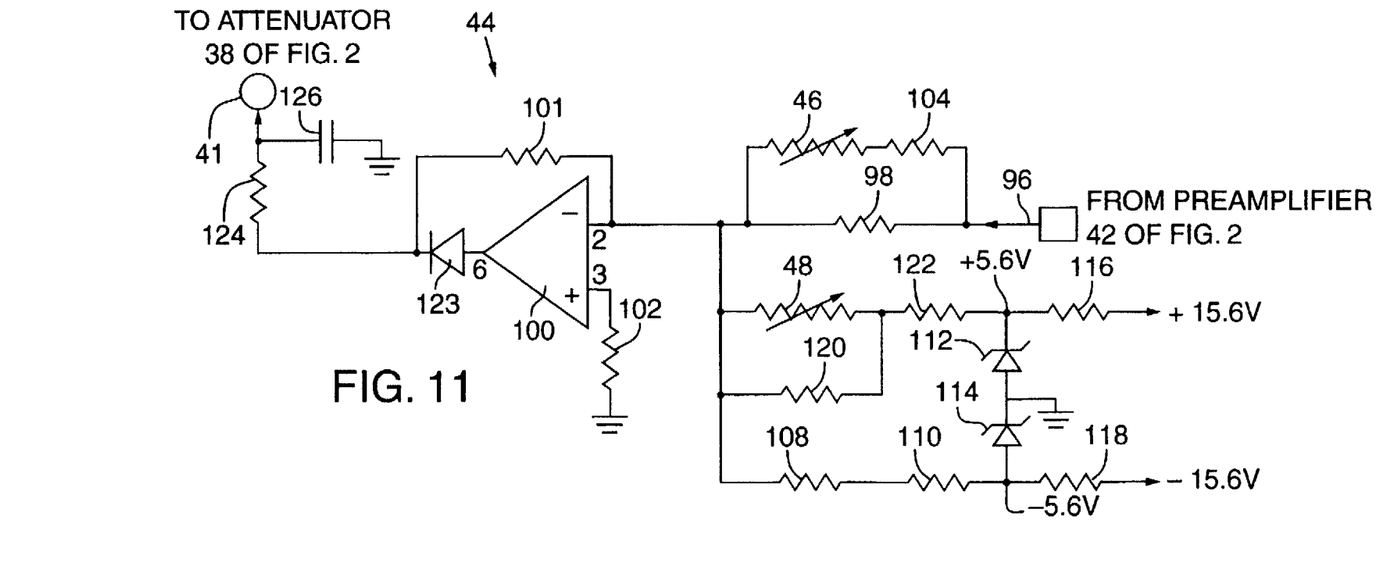
FIG. 11 is a temperature compensation circuit for the PIN attenuators in the circuits of FIGS. 2 and 3.
Figure 12:
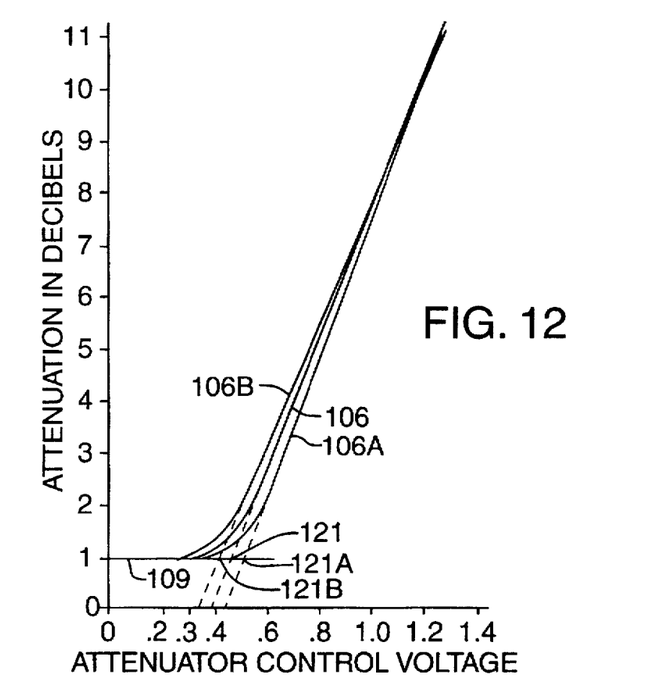
FIG. 12 shows the attenuation characteristic curves of PIN attenuators at different temperatures.

The received microwave signal $f_2$ after passing through the moist test material 1 is passed from the connector 20 of a receiving antenna 35 through another isolator 37 to the input of a PIN diode variable attenuator 38 which further attenuates the signal to produce a constant signal level at the input to the signal detector 39 connected through a hybrid divider 54 to the output of such attenuator. This constance is achieved by comparing the attenuated received signal from the signal detector 39 after it is amplified by preamplifier 36 to equal the reference signal from the reference detector 34 which are applied to the two inputs of a high gain differential amplifier 40 to produce an attenuated output signal, Vo, proportional to the attenuation of the test material as given in Equation 7. It should be noted that the preamplifier 36 may be combined as a part of the differential amplifier 40. The output signal, Vo, of differential amplifier 40 is also transmitted through a preamplifier 42 and a temperature compensation circuit 44 including a pair of thermistors 46 and 48 to a control terminal 41 of the attenuator 38, making a closed loop, negative feedback arrangement. The temperature compensation circuit 44 is shown in FIG. 11 and operates in a manner hereafter described to adjust the attenuation characteristic of the PIN diode attenuator 38 to compensate for temperature changes, as shown in FIG. 12. As a result of such negative feedback, any difference between the two compared signals at the inputs of amplifier 40 is applied to control terminal 41 of attenuator 38 and causes a change in attenuation of the received signal by the PIN diode attenuator as needed to bring the microwave signal level at the input of signal detector 39 to the desired constant value. The same circuit operation occurs when the first microwave signal of high frequency $f_1$ of, for example, 10.7 GHz is transmitted from source 30' through coupler 31' and isolator 32' to the coaxial connector 15 of transmission antenna 33. Therefore, such operation of the other attenuation circuit including isolator 37', PIN diode variable attenuator 38', signal detector 39', preamplifier 36', reference detector 34', differential amplifier 40', preamplifier 42' and temperature compensation circuit 44' to produce the second attenuated output signal Vo' will not be described.

Clearly, if there is an increase of attenuation by the moist test material 1 there will be an equal decrease of attenuation by the PIN diode attenuators 38 and 38'. Since the attenuation by each PIN diode attenuator is a direct function of the output signal Vo or Vo' fed to its control input 41 or 41', these output signals provide a direct measure of the attenuations "a" in the moist material at frequencies $f_2$ and $f_1$, respectively. Thus, the difference between attenuation a and attenuation a' obtained by subtracting Vo' from Vo is proportional to the amount of moisture in the test material.

Figure 3:
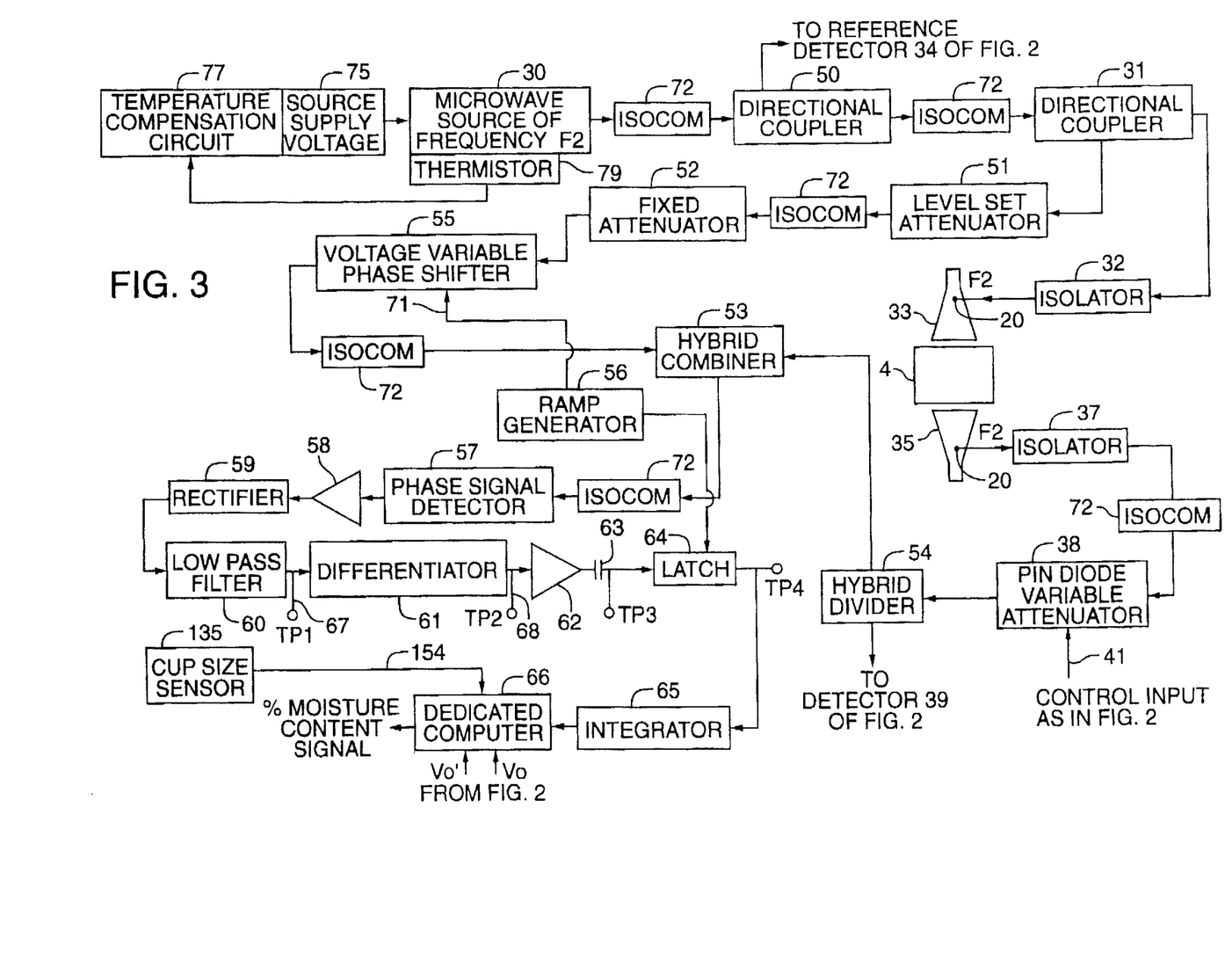
FIG. 3 is a schematic diagram showing the electrical circuit of such portable instrument for measurement of the phase shift of a received microwave signal to determine the density of the test material, and to combine it with the attenuation measurements of FIG. 2 in order to determine the percent of moisture content in a second embodiment of the microwave moisture measurement instrument of the present invention.

For phase measurement in FIG. 3 using low frequency microwave signal $f_2$ to determine the density of the test material, all the components of the corresponding circuit of FIG. 2 are used as described above for attenuation measurement and directional coupler 31 is employed to provide a phase reference signal and a hybrid divider 54 is added between the PIN diode attenuator 38 and the signal detector 39 in FIG. 2. These two added components are fixed passive devices so that their addition leaves the operation of the attenuation loop effectively unchanged.

FIG. 3 is a schematic block diagram of the phase measuring circuit used in one embodiment of the invention. Microwave source 30 transmits microwave signal $f_2$ of low frequency of 5.86 GHz through the directional coupler 50 and coupler 31 which feeds a small fraction (between 0.1% and 1.0%) of the signal through a level set attenuator 51, a fixed attenuator 52 of 21 decibels attenuation and a voltage variable phase shifter 55 to one input of a hybrid combiner 53 to provide a phase reference signal to this combiner. The microwave source 30 is connected to a DC power supply voltage source 75 of about −12 volts which is battery operated and is provided with a temperature compensation circuit 77 including a thermistor 79 mounted in heat conduction to the microwave signal source to maintain the frequency of such signal substantially constant by varying the power supply voltage in response to temperature changes of the source. Thus an increase in source temperature causes an increase in source frequency while an increase in source supply voltages causes a decrease in source frequency.

On the receiving side, the output of PIN diode variable attenuator 38 is connected to the input of added hybrid divider 54 which feeds half the received signal to the attenuation loop 39, 36, 40, 42, 44 and 41 of FIG. 2 and the other half of such received signal is fed from divider 54 to one input of a hybrid combiner 53 whose other input is connected to the output of a voltage variable phase shifter 55.

The voltage variable phase shifter 55 is arranged to be swept periodically through a full 360° phase change by the ramp shaped voltage applied to control terminal 71 by a ramp generator 56. As a result, the phase of the phase shifted received signal applied by shifter 55 to the second input to the hybrid combiner 53 is swept periodically through 360°.

Figure 4:
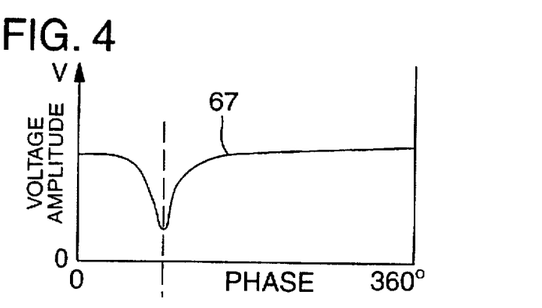
FIG. 4 shows the electrical signal produced at test point TP1 in FIG. 3, plotted through one 360° phase sweep of the phase shifter of FIG. 3.

The hybrid combiner 53 of FIG. 3 combines the two input signals so that its combined output signal is the vector sum of such two input signals. If, therefore, the two input signals are of equal amplitude there will be one point in the 360° sweep where the two signals are 180° out of phase with each other and the hybrid combiner output will dip to a minimum amplitude. The operation of the attenuator loop 54, 39, 36, 40, 42, 44, 41 shown in FIG. 2 of attenuator 38 ensures that the signal level at the output of the attenuator remains almost constant and is a near constant fraction of the phase reference output signal of the directional coupler 31. The level set attenuator 51 is therefore adjusted to make the amplitudes of the two input signals of the hybrid combiner 53 near to equal. The output from the hybrid combiner 53 passes through the phase signal detector 57 which gives a detected output signal whose amplitude is proportional to the amplitude of the combined output signal of the hybrid combiner and which therefore goes through a sharp minimum at one point in each 360° sweep of the ramp generator. It should be noted that each sweep can be less than 360° if it includes the sharp minimum. This detected signal is amplified by amplifier 58, rectified by a full wave rectifier 59 and filtered by low pass filter 60 to give a phase shift indication signal 67 at test point No. 1 as shown graphically in FIG. 4. The low pass filter 60 between the rectifier 59 and TP1 serves to clean up this signal by removing noise and unwanted components from the signal.

Figure 5:
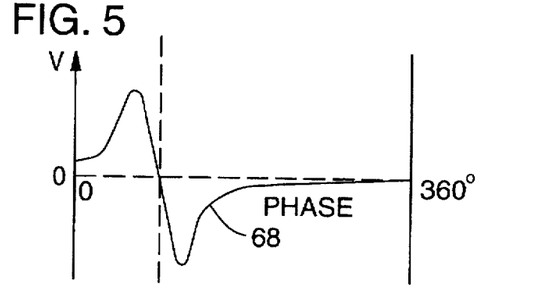
FIG. 5 shows the electrical signal produced at TP2 in FIG. 3, plotted through the same 360° phase sweep of FIG. 4.
Figure 6:
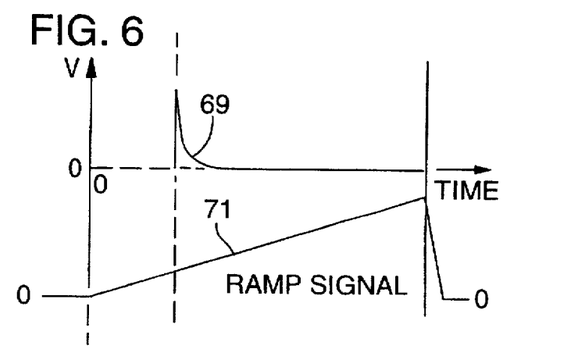
FIG. 6 shows the electrical pulse produced at TP3 in FIG. 3, and the ramp voltage produced by the ramp generator of FIG. 3.
Figure 7:
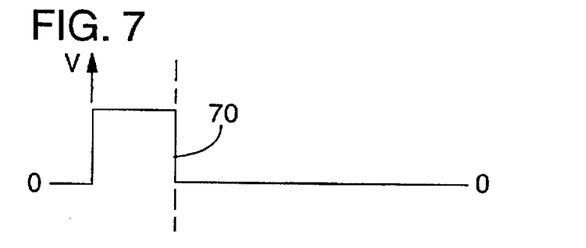
FIG. 7 shows the electrical signal produced at TP4 in FIG. 3 shown on the same time scale as the signals of FIG. 6.

A differentiator circuit 61 converts the signal from TP1 to the differentiated phase shift indication signal 68 of the waveform indicated in FIG. 5 at TP2 in which there is a sharp transition through zero. The comparator 62 and capacitor 63 serves to convert this signal into a sharp positive spike pulse 69 at TP3 corresponding to the zero crossing of signal 68 and applies such spike pulse to one input of the latch 64 and as shown in FIG. 6. The other input of the latch 64 is a second sharp spike pulse corresponding to the start of the ramp voltage signal 71 which comes from the ramp generator circuit 56 so that a positive rectangular latch output pulse 70 produced at TP4 is initiated at the start of each ramp and is terminated by spike pulse 69 at the phase signal minimum point as shown in FIG. 7. This is repeated for each repetitive 360° sweep of the ramp generator and so produces a pulse train with pulses 70 of constant amplitudes and variable pulse widths with their pulse width proportional to the phase shift of the minimum point in signal 67 corresponding to the output from the hybrid combiner 53. The integrator 65 which integrates this pulse train therefore gives a phase shift output signal, $V_p$, whose voltage level is proportional to this phase shift.

The phase shift signal $V_p$ is approximately proportional to the density of the test material in the following equation for the moisture range of zero to four percent moisture which applies to foundry sand.

$$\log \epsilon_m = C_1 W d + C_2 d \qquad \text{Equation 8}$$

where $\epsilon_m$ is the dielectric constant of the mixture of air, water and sand in the test material, $C_1$ and $C_2$ are constants related to the dielectric constants of water and sand, W is the percent of water and d is the density of the test material.

The zero level of this phase shift output signal $V_p$ corresponds to the phase of the received signal which would produce a hybrid combiner output signal minimum at the start of each ramp. This can be adjusted to a desired minimum corresponding, for example, to some minimum density at zero percent water by adjustment of a pre-settable phase shifter (not shown) provided at the input of attenuator 38. The phase shift output signal $V_p$ of integrator 65 and the attenuation output signals Vo and Vo' of the differential amplifiers 40 and 40' of FIG. 2 are applied to the inputs of a dedicated computer or data processor 66, such as a general purpose digital computer, which is programmed to combine such signals in accordance with Equations 6, 7 and 8 to produce a percent moisture content signal at the output of such data processor which indicates the amount of moisture in the test material 1. The dedicated computer 66 of FIG. 3 provides three functions. First, detailed operating instructions to the operator who may have no instrumentation training or experience. This includes control by the computer of a suitable indicator display to indicate use of the correct cup size for the substance being measured in response to the output of a cup size sensor circuit 135 hereinafter discussed. Second, control of power supply battery charging. Third, preset input by software into the computer, of all formulae or equations and all constants required for the calculation of the desired output measurement signals, for each of the test materials. In general these output measurements relate to "moisture" but may also include "density" or may include "conductivity", either ionic or metallic or carbon.

Figure 13:
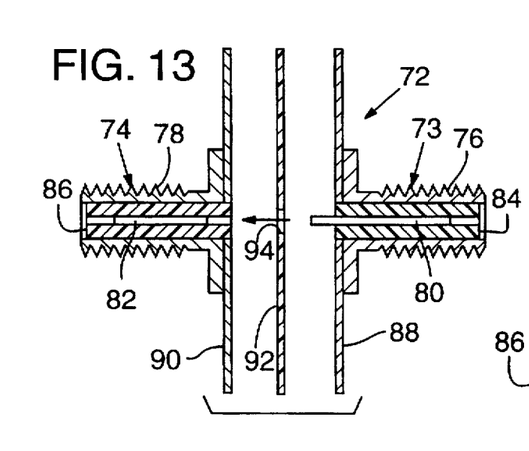
FIG. 13 is an exploded view of a microwave isolation connector in accordance with the present invention.
Figure 14:
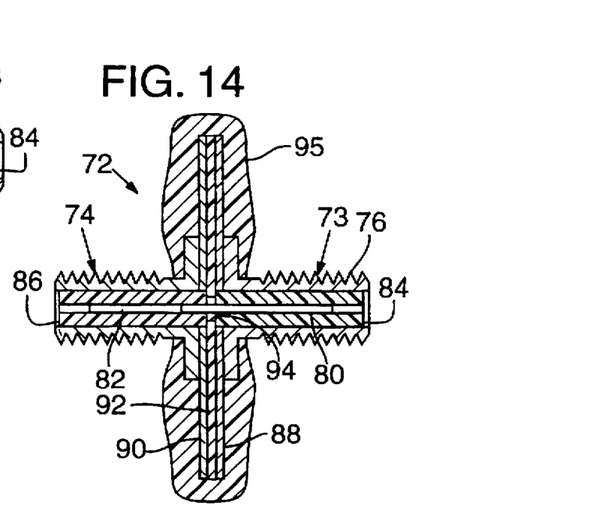
FIG. 14 is an assembled view in cross-section of the microwave isolation connector of FIG. 13.

A plurality of microwave connectors 72 each hereinafter called an "Isocom", are provided at various positions throughout the microwave circuits of FIGS. 2 and 3 to isolate the outer conductors of interconnected microwave waveguides, such as coaxial cables, from DC voltage coupling while allowing low impedance AC voltage coupling of microwave frequency signals. The microwave connector 72 is shown in the exploded view and the assembled view of FIGS. 13 and 14 and preferably includes two coaxial cable connectors 73 and 74, such as SMA type connectors for printed circuit boards. Each of the connectors 73 and 74 includes an outer conductor 76, 78 and an inner conductor 80, 82 separated by an insulator sleeve 84, 86 of Teflon or other suitable plastic. A pair of conductor disks 88, 90 of brass or other suitable metal are soldered to the mounting flanges of the outer conductors 76 and 78, respectively, and may have a diameter of 2.0 cm. The conductor disks 88, 90 are separated by an insulator disk 92 of mica or other suitable high dielectric material of somewhat greater diameter than the conductor disks and having a thickness of about 0.013" to insulate the conductor disks from each other. The insulator disk 92 is provided with a central opening 94 therethrough of sufficient diameter to allow the inner conductor 80 of connector 73 to pass through such disk and interconnect with the inner conductor 82 of connector 74 by a plug and socket type connection and by soldering after assembly or by a single conductor interconnecting both connectors. After the microwave connector 72 is assembled as shown in FIG. 14 the mechanical contact of the conductor disks 88, 90 with the insulator disk 92 is maintained by epoxy resin potting material 95 around such disks to provide the connector with an outer diameter of 3 cm and a maximum connector length of 1.9 cm. It should be noted that the outer conductors 73 and 74 are isolated by the insulator disk 92 to prevent DC voltage coupling between such outer conductors but are capacitively coupled through such disk to provide a low impedance AC voltage coupling at microwave frequencies but a high impedance coupling at lower modulation frequencies. Thus for brass conductor disks 88, 90 of 2 cm diameter and 0.016" thickness separated by a mica insulator disk 92 of 0.013" thickness and a dielectric constant of 7, the calculated capacitance is 50 picofarads. This capacitive connection had a DC resistance greater than 10 megohms, a high AC impedance of 300 kilohms or more at modulation frequencies of 10 kHz to 20 kHz and low AC impedance of less than 1 ohm and less than 0.25 decibel attenuation of microwave signals in the range of 5.8 GHz to 10.7 GHz.

The microwave connectors 72 solve the problem of most microwave waveguides which use their outer conductor both as a metal shield to contain the microwaves and as a common return or ground return which therefore interconnects almost all the microwave components of a circuit. This results in ground loops for signals of different frequencies and phase with attendant interference and spurious signal problems. A portable microwave instrument cannot use separate power supplies and isolation transformers to solve this problem because of the added weight and size and because it uses a battery power supply.

The temperature compensation circuits 44 and 44' for the PIN attenuators 38 and 38' of FIG. 2, are shown in FIG. 11 to each include a first thermistor 46 and a second thermistor 48 whose resistance varies with temperature. The input terminal 96 of the circuit 44 is connected through an input coupling resistor 98 of 301 kilohms to the inverting input of an operational amplifier 100 with a negative feedback resistance 101 of 100 kilohms and whose non-inverting input is connected to ground through a bias resistor 102 of 25 kilohms. The first thermistor 46 is connected in series with a fixed resistor 104 of 143 kilohms and this series impedance is connected in parallel with the input coupling resistor 98. The operating characteristic of the PIN attenuators 38 and 38' is shown in FIG. 12 by curves of attenuation in decibels along the vertical axis and attenuator control voltage at control input 41 along the horizontal axis. As a result of changes in the resistance of the thermistor 46 with changes in temperature of the PIN attenuator 38 on which it is mounted, the slope of the attenuation operating characteristic curve 106 at 23.7° C. changes as shown by curves 106A and 106B at 0° C. and 41.5° C. to compensate for such changes, as shown in FIG. 12.

For the purpose of temperature compensation, the PIN attenuation curve is approximated by two straight lines; a short horizontal line 109 representing zero PIN attenuation, where the PIN control voltage is below the point where PIN diode current starts, and a rising sloping straight line 106 of constant slope following most of the increase of PIN attenuation with increasing control voltage and control current. Where these two straight lines intersect is termed the "break point". The slopes of the three attenuation curves 106, 106A and 106B at different temperature of 23.7° C., 0° C. and 41.5° C., respectively, when projected downward intersect the horizontal straight line portion 109 at 1 decibel attenuation which corresponds to "the insertion loss" of the PIN attenuator, at break points 121, 121A and 121B, respectively.

A shunt resistance network including a pair of series connector resistors 108 and 110 of 3.65 kilohm and 90.9 kilohms, respectively, is connected from the inverting input of the amplifier 100 to a source of DC reference voltage of −5.6 volts at the common connection of Zener diode 114 and resistor 118 of 3.32 kilohms from a DC voltage source of −15.6 volts. The second thermistor 48 is connected in parallel with a resistor 120 of 4.75 kilohms and this parallel impedance is connected in series with a shunt resistor 122 of 100 kilohms from the inverting input of amplifier 100 to a source of DC reference voltage of +5.6 volts at the common connection of a Zener diode 112 and a resistor 116 of 3.32 kilohms from a DC voltage source of +15.6 volts. As a result of changes in the resistance of the second thermistor 48 with changes in temperature of the PIN attenuator 38 the break voltage point 121 of the attenuation curve 106 changes from 0.465 volt as shown in FIG. 12 to break points 121A and 121B of 0.510 volt and 0.420 volt for attenuator curves 106A and 106B to compensate for such changes. It should be noted that the current flowing through the thermistors 46 and 48 is small enough to have a negligible effect on their temperature.

The output of the operational amplifier 100 is connected through a diode 123 in series with a coupling resistor 124 of 1.8 kilohms to the control terminal 41 of the attenuator 38 to change the attenuation in accordance with the output voltage signal applied to such control terminal, as shown in FIG. 12. A shunt capacitor 126 of 0.47 microfarads is connected from the output terminal 41 and ground. As shown in FIG. 12 changes in the control voltage applied to the control input 41 of the attenuator 38 change the attenuation of the received microwave signal transmitted through such attenuator.

Figure 8:
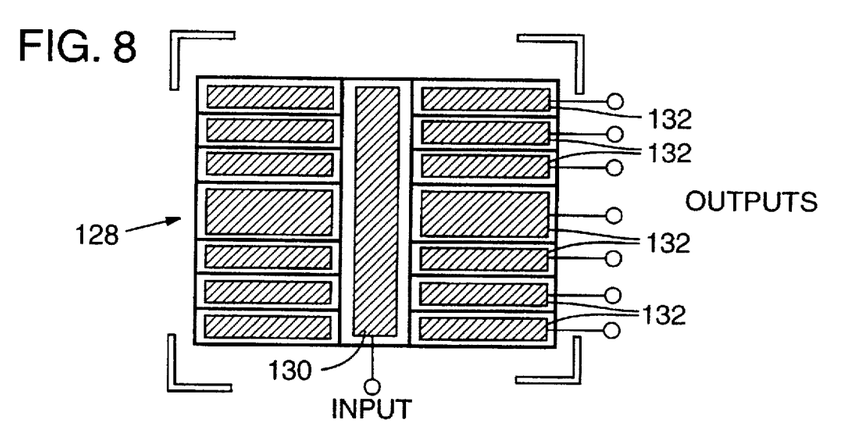
FIGS. 8 and 9 show test container size sensor apparatus using different patterns of conductive strips to indicate the selected container sizes.
Figure 9:
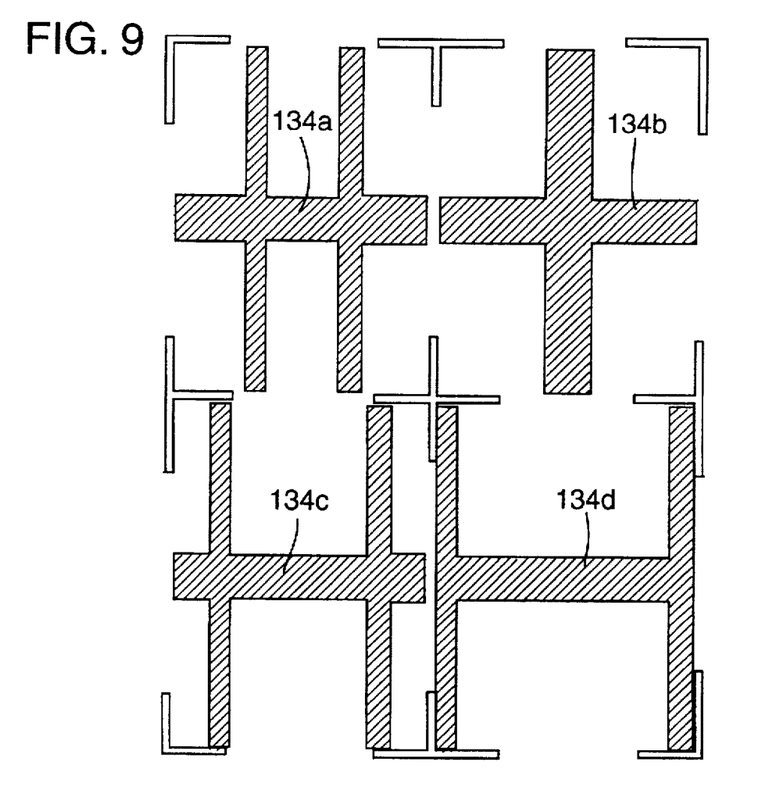

As shown in FIG. 8 the test container size sensor includes a container holder which employs a sensor pattern 128 of conductive strips including a common input strip 130 and a plurality of insulated output strips 132. The output strips 132 are selectively coupled to the input strip 130 through four different test patterns of conductor strips 134A, 134B, 134C and 134D on the bottoms of the four different size test containers, as shown in FIG. 9. A number of different size test containers 4 are necessary because of the wide range of moisture contents to be measured with high accuracy. Thus for very wet material a large container should not be used because of too high attenuation of the received signal so that its amplitude is too small or inaccurate for accurate moisture measurement. On the other hand, for low moisture material a small container should not be used because of too little attenuation of the signal.

Figure 10:
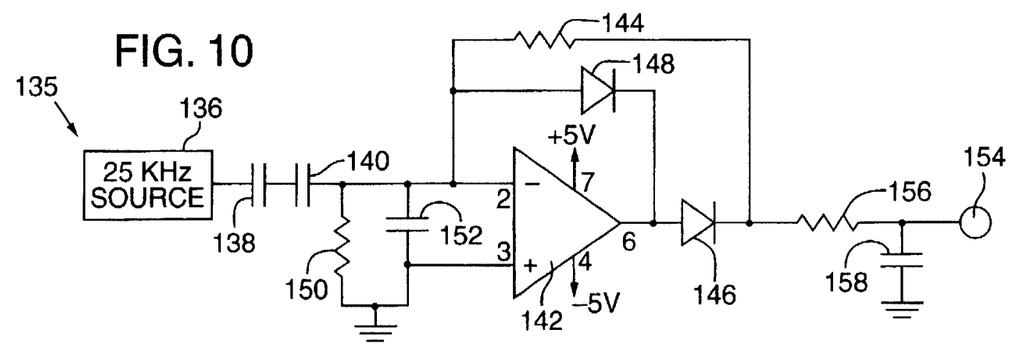
FIG. 10 is a container size sensor circuit connected to the sensor apparatus of FIGS. 8 and 9.

A test container sensor circuit 135 is shown in FIG. 10 and includes an AC signal source 136 of 14 to 25 kHz and a peak-to-peak voltage of about 10 volts which is applied to the input strip 130 of the sensor pattern 128. The test signal is coupled to the sensor circuit amplifier 142 by a first effective capacitance 138 between such input strip and the selected container pattern 134 and by a second effective capacitance 140 between the selected container pattern and the corresponding output strip 132. The selected container size signal is transmitted through capacitance 140 to the inverting input of an operational amplifier 142 whose non-inverting input is connected to ground. A negative feedback resistor 144 of 3.6 megohms is connected from the output of the amplifier 142 through an output coupling diode 146 to the inverting input of such amplifier. A diode 148 is connected from the inverting input to the output of amplifier 142 to discharge the capacitances 138 and 140 through coupling diode 146. A shunt impedance including a resistor 150 of 68 kilohms and a parallel capacitor 152 of 82 picofarads is connected from the inverting input of amplifier 142 to ground to reduce stray coupling output signals. The container sensor output signal is transmitted from the output of amplifier 142 to an output terminal 154 through a smoothing filter including a coupling resistor 156 of 10 kilohms and a shunt capacitor 158 of 22 nanofarads. The output terminal 154 of the cup size sensor circuit 135 of FIG. 10 is connected to the input of the computer 66 of FIG. 3.

There are four of these container size sensor circuits, one for each of the four container cup sizes having signal path lengths of 3", 2", 1", ½". When a cup is installed, the circuit for its size is required to give an output voltage signal to the computer at output 154 which will be read as a "high"; this means that it must be greater than 3 volts. The other three sensor circuits are each, at the same time, required to give an output voltage signal which will be read as a "low" and must be less than 1 volt.

The sensor circuit acts as a "perfect detector" which, with the capacitor 158 and resistor 156 smoothing filter, yields a steady DC output voltage to the computer.

C1 is the effective capacitance 138 between the center strips of the circuit boards in the cup well and the cup.

C2 is the effective capacitance 140 between the cup size strips of the two circuit boards.

C1 and C2 have effective capacitances given by:

$$C = 8.85 \frac{A\epsilon}{d} \text{ picofarads}$$

where A is the area of the coupling strips, d is the distance between the cup strips and the well strips, and $\epsilon$ is the dielectric constant of the circuit board insulating material which separates the cup strips from the well strips.

The capacitance values of C1 and C2 in the prototype are 6.5 picofarads each in the cup sensor circuit for the cup size that has been installed, so that together they provide an input capacitance "C" of 3.25 picofarads.

During each cycle of the 25 kHz input signal, this capacitance is charged to the peak negative voltage by current drawn through the 144 feedback resistor $R_f$ and is then discharged to the peak positive voltage through the feedback 148 diode DC. Thus, the charge "q" fed through $R_f$ effects a voltage change across C equal to the peak-to-peak input signal "V".

The charge "q" to the capacitance C=3.25 picofarads with a 10 volt peak-to-peak input signal "V" is thus:

$$q=C \times V=32.5 \text{ micro micro coulombs}$$

This charge, drawn through the 144 feedback resistor $R_f$ once every cycle of the 25 kHz input signal, means that there is a mean current "i" through $R_f$ and $$i=q/\tau=0.8125 \text{ micro Amp}$$

where $\tau$ is the period of the input signal, equal to $\frac{1}{25000}$; this current "i" will produce a mean smoothed output voltage signal "E" of:

$$E=i \times R_f=2.925 \text{ volt}$$

Due to stray couplings, much of it due to other stray frequencies, there is a small additional input signal, other than through C1 and C2. With no cup installed, this produces an output signal which was measured to be about 1.3 volt. To reduce this, the capacitor 152 and the resistor 150 were added to the sensor circuit at the operational amplifier input; they have reduced this stray output signal to about 0.45 volt. Since this is present at all times it adds to the cup signal to yield a total output for the installed cup of 3.375 volt, which certainly registers as a "high" in the computer.

In the three sensor circuits for cup sizes other than the one installed, the input capacitor C1 is still 6.5 picofarads, as for the installed cup, but C2 is greatly reduced, both because the installed cup does not have the cross strips for the other cup sizes and because of the shielding effect of the grounded conductors which have been added to the well circuit board, between all the strips, for this purpose, coupled with the use of shielded interconnecting leads from the strips to the cup sensor circuits. The result is that the net input capacitance to these other sensor circuits is only about 0.38 picofarads, giving only about 0.34 volt output to combine with the approximately 0.45 volt due to stray input signals; this gives a net output signal to the computer of less than 0.8 volt which certainly registers as a "low".

There was one further problem affecting the cup sensing. If the material being measured in the cup is electrically conducting, or has some electrical conductivity, (as does foundry molding sand, due to presence in it of free carbon atoms) this could add appreciable stray couplings between the sensing strips, causing false cup size signals. The means which has been found to be effective to obviate this is to add a spacer between the bottom of the cup and the circuit board carrying the sensing strips so as to make the between the measured material and the sensing strips at least ⅛".

It will be obvious to those having ordinary skill in the art that many changes may be made in the above described preferred embodiment of the present invention. Therefore, the scope of the present invention is to be determined by the following claims.

I claim:

1. Microwave apparatus for measuring the moisture content of test materials, comprising:

microwave transmitting means including microwave signal source for applying two microwave input signals of two different frequencies to at least one first microwave antenna for transmitting two microwave beams corresponding to said input signals, and reference signal source for supplying two microwave reference signals with a constant phase relationship to and of the same frequency as said two input signals;

testing device for providing a test container of a predetermined volume of test material in the path of the two microwave beams so that the beams are transmitted through the test material and a portion of the energy of each beam is absorbed by the test material and any moisture therein;

microwave receiving means including at least one second microwave antenna for receiving the two microwave beams after they are transmitted through the test material to produce two received microwave signals of said two different frequencies;

variable attenuators for attenuating each of said two received signals by a variable amount in response to the application of control signals to said attenuators to provide two attenuated received signals;

temperature compensation circuit including at least one thermistor for correcting changes in the attenuated received signals due to changes in temperature of each of the attenuators; and comparator circuit for comparing detected modulation signals corresponding to each of the two attenuated received signals and the respective reference signal of the same frequency to produce an output signal which is employed for production of the control signals for the attenuators to vary the attenuation of each received signal until it equals a predetermined portion of its corresponding reference signal.

2. Microwave apparatus in accordance with claim 1 in which the variable attenuators are PIN attenuator devices whose impedance varies with the amplitude of the control signal.

3. Microwave apparatus in accordance with claim 2 in which the PIN attenuator devices are diodes and the temperature compensation circuit includes two thermistors which each compensate for changes in the break point voltage of the PIN diode and the slope of the attenuation curve of said diode with changes in temperature of the diode.

4. Microwave apparatus in accordance with claim 3 in which one thermistor is connected in parallel with a coupling resistance having its input terminal connected to the output of a control signal amplifier for the attenuator and the second thermistor is connected between the output terminal of said coupling resistance and a source of reference voltage.

5. Microwave apparatus in accordance with claim 4 in which the output of the coupling resistance is connected to the input of an operational amplifier whose output is connected to the control terminal of the PIN diode.

6. Microwave apparatus in accordance with claim 1 in which the testing device includes a holder for the test container which has an electrical sensor for sensing the size of the test container.

7. Microwave apparatus in accordance with claim 6 in which the sensor includes a plurality of conductive strips arranged in a pattern which are selectively connected to different test patterns of conductive strips on containers of different sizes to sense the size of the selected container and produce a corresponding sensor output signal; and computer means for automatically producing a container size indication in response to the receipt of the sensor output signal.

8. Microwave apparatus in accordance with claim 7 in which the sensor includes a common input strip having an input terminal connected to an AC test signal source which is transmitted through the test pattern on the selected container to an output strip on the sensor.

9. Microwave apparatus in accordance with claim 1 in which the microwave sources are each connected to at least one common microwave signal connector comprising first and second microwave connections each having an outer and inner conductor separated by an insulator, said inner conductors of said first and second connectors being coupled together by a common connection and said outer conductors of said first and second connectors being separated by an insulator plate so that DC signals are not transmitted between said outer conductors but AC signals of microwave frequency are transmitted between said outer conductors with low attenuation.

10. Microwave apparatus in accordance with claim 9 in which the first and second microwave connectors are coaxial cable connectors with their outer conductors each connected to a metal disk of larger diameter than the outer conductor, and the insulator plate is fixed between said metal disks to insulate them and is provided with a central opening through which extends the inner conductor of at least one cable connector.

11. Microwave apparatus for measuring the moisture content of test materials, comprising:

microwave transmitting means including microwave signal source for applying two microwave input signals of two different frequencies to at least one first microwave antenna for transmitting two microwave beams corresponding to said input signals, and reference signal source for supplying two microwave reference signals with a constant phase relationship to and of the same frequency as said two input signals;

testing device for providing a test container of a predetermined amount of test material in the path of the two microwave beams so that the beams are transmitted through the test material and a portion of the energy of each beam is absorbed by the test material and any moisture therein;

microwave receiving means including at least one second microwave antenna for receiving the two microwave beams after they are transmitted through the test material to produce two received microwave signals of said two different frequencies;

variable attenuators for attenuating each of said two received signals by a variable amount in response to the application of control signals to said attenuators to provide two attenuated received signals;

electrical sensor including a holder for sensing the size of the test container; and comparator circuit for comparing detected modulation signals corresponding to each of the two attenuated received signals and the respective reference signal of the same frequency to produce an output signal which is employed for production of the control signals for the attenuators to vary the attenuation of each received signal until it equals that of its corresponding reference signal.

12. Microwave apparatus in accordance with claim 11 in which the sensor includes a plurality of conductive strips arranged in a test pattern which are selectively connected to different test patterns of conductive strips on containers of different sizes to sense the size of the selected container and produce a corresponding sensor output signal.

13. Microwave apparatus in accordance with claim 12 in which the sensor includes a common input strip having an input terminal connected to an AC test signal source which is transmitted through the test pattern on the selected container to an output strip on the sensor.

14. Microwave apparatus in accordance with claim 11 that is a portable battery operated instrument and which also includes temperature compensation circuit including at least one thermistor for maintaining the frequency of at least one microwave input signal substantially constant by changing the source voltage to compensate for temperature changes in the source.

15. Microwave apparatus in accordance with claim 11 in which the variable attenuators are PIN attenuator devices whose impedance varies with the amplitude of the control signal.

16. Microwave apparatus in accordance with claim 15 in which the PIN attenuator devices are diodes each having a temperature compensation circuit which includes two thermistors to compensate for changes in the break point voltage of the PIN diode and the slope of the attenuation curve of said diode with changes in temperature of the diode.

17. Microwave apparatus in accordance with claim 16 in which one thermistor is connected in parallel with a coupling resistance having its input terminal connected to the output of a control signal amplifier for the attenuator and the second thermistor is connected between the output terminal of said coupling resistance and a source of reference voltage.

18. Microwave apparatus in accordance with claim 11 which includes phase adjustment means for varying the phase of one received signal relative to its reference signal of the same frequency;

combiner means for combining the phase shifted received signal and its reference signal to produce a combined signal whose amplitude is minimum when the phase shift is about 180°;

detector means for detecting the combined signal to produce a phase shift indicator signal; and computer means for producing a moisture indicator signal corresponding to said phase shift indicator signal.

19. A microwave signal connector apparatus comprising:

first and second microwave connectors each having an outer and inner conductor separated by an insulator, said inner conductors of said first and second connectors being directly connected together by a common connection; and an insulator plate of non-magnetic material positioned in a narrow width gap between said outer conductors of said first and second connectors for high attenuation of low frequency modulation signals and elimination of DC signals so they are not transmitted between said outer conductors to prevent ground loops in the outer conductors, but AC signals of microwave frequencies are transmitted between said outer conductors through a low impedance capacitance coupling with little attenuation.

20. Microwave apparatus in accordance with claim 19 in which the first and second microwave connectors are coaxial cable connectors with their outer conductors each connected to a metal disk of larger diameter than the outer conductor, and the insulator plate is fixed between the two metal disks to insulate them and is provided with a central opening through which extends the inner conductor of said cable connectors.

* * * * *